US008703823B2

(12) United States Patent  
Salehani

(10) Patent No.: US 8,703,823 B2
(45) Date of Patent: Apr. 22, 2014

(54) METHODS FOR TREATMENT OF MIGRAINE AND SYMPTOMS THEREOF

(76) Inventor: Foad Salehani, Los Angeles, CA (US)

(*) Notice: Subject to any disclaimer, the term of this patent is extended or adjusted under 35 U.S.C. 154(b) by 1194 days.

(21) Appl. No.: 12/211,619

(22) Filed: Sep. 16, 2008

(65) Prior Publication Data

US 2009/0018205 A1  Jan. 15, 2009

Related U.S. Application Data

(62) Division of application No. 10/871,847, filed on Jun. 17, 2004, now abandoned.

(51) Int. Cl.
| | | |
|---|---|---|
| *A01N 37/18* | (2006.01) | |
| *A61K 31/165* | (2006.01) | |
| *A01N 33/02* | (2006.01) | |
| *A61K 31/135* | (2006.01) | |

(52) U.S. Cl.
USPC .......................................... 514/622; 514/648

(58) Field of Classification Search
USPC ................................................ 514/622, 648
See application file for complete search history.

(56) References Cited

U.S. PATENT DOCUMENTS

| | | |
|---|---|---|
| 4,443,464 A | 4/1984 | Biedermann et al. |
| 4,749,700 A | 6/1988 | Wenig |
| 5,036,078 A | 7/1991 | Coates |
| 5,538,959 A | 7/1996 | Mauskop |
| 5,721,252 A | 2/1998 | Audia et al. |
| 5,744,482 A | 4/1998 | Cohen et al. |
| 5,872,145 A | 2/1999 | Plachetka |
| 6,077,539 A | 6/2000 | Plachetka et al. |
| 6,251,935 B1 | 6/2001 | Schoenen et al. |
| 6,255,334 B1 | 7/2001 | Sands |
| 6,380,242 B1 | 4/2002 | Arora et al. |
| 6,402,678 B1 | 6/2002 | Fischell et al. |
| 6,465,517 B1 | 10/2002 | Van Der Zee |
| 6,476,042 B1 | 11/2002 | Harrison |
| 6,479,551 B1 | 11/2002 | Plachetka et al. |
| 6,503,884 B1 | 1/2003 | Ehrenberg et al. |
| 6,635,639 B2 | 10/2003 | Arora et al. |
| 6,685,951 B2 | 2/2004 | Cutler |
| 6,716,837 B1 | 4/2004 | Edwards et al. |
| 2002/0055495 A1 | 5/2002 | Jannetta |
| 2003/0008892 A1 | 1/2003 | Coe et al. |
| 2004/0005354 A1 | 1/2004 | Gregory et al. |
| 2004/0147510 A1 | 7/2004 | Landau et al. |
| 2005/0282879 A1 | 12/2005 | Salehani |

FOREIGN PATENT DOCUMENTS

GB       1442159    *  7/1976

OTHER PUBLICATIONS

Adelman et al. (Headache, 44, 3, p. 271-285, Mar. 2004).*
Tigan (Monarch Pharmaceuticals, Dec. 2001, Product Description).*
Aube (Neurology, 53, S26-28, 1999).*
Anonymous (2004). "Migraine," located at <http://en.wikipedia.org/wiki/Migraine>, last visited on Apr. 28, 2004, three pages.
Anonymous (Date Unknown). "Tigan: Prescription Drug Reference from HealthSquare.com" located at <http://www.healthsquare.com/newrx/tig1443.html> last visited on Apr. 13, 2004, five pages.
Diamond, M. (2003). "Women's Issues in Migraine," National Headache Foundation, pp. 1-10.
Diamond, S. (Jan. 2001). "A Fresh Look at Migraine Therapy," Postgraduate Medicine 109(1):49-60.
Drake, R. et al. (Jan. 2001). "Impact of an Antiemetic Protocol on Postoperative Nausea and Vomiting in Children," Paediatric Anaesthesia 11(1):85-91.
Fanciullacci, M. et al. (2000). "Dopamine Involvement in the Migraine Attack," Functional Neurology 15(Supp 3):171-181.
Flake, Z.A. et al. (Mar. 1, 2004). "Practical Selection of Antiemetics," American Family Physician 69:1169-1174, located at <http://www.aafp.org/afp/20040301/1169.html>, last visited on Apr. 14, 2004, 9 pages.
Friedman, B.W. et al. (Jun. 2006). "A Clinical Trial of Trimethobenzamide/Diphenhydramine Versus Sumatriptan for Acute Migraines," Headache 46:934-941.
Gennaro, A.R. ed. (2000). Remington: The Science and Practice of Pharmacy 20th Edition, Lippincott, Williams & Wilkins, pp. xiv-xv. (Table of Contents Only.).
Gylys, J.A. et al. (1988). "BMY-25801, an Antiemetic Agent Free of D2-Dopamine Receptor Antagonist Properties," The Journal of Pharmacology and Experimental Therapeutics 244(3):830-837.
Hannon, J. et al. (2002). "Serotonin Receptors and Systems: Endless Diversity?" Acta Biologica Szegediensis 46(1-2):1-12.
Lipton, R.B. et al. (2001). "Prevalence and Burden of Migraine in the United States: Data From the American Migraine Study II," Headache 41(7):646-657.
McMahon, C. et al. (Feb. 2001). "The Treatment of Nausea and Vomiting in Pregnancy (NVP)," Nausea and Vomiting vol. 8, No. 2, located at <http://www.fetal-exposure.org/NAUSEA.html>, last visited on Apr. 13, 2004, 11 pages.
Monarch Pharmaceuticals (Dec. 2001). Product Description of Tigan® (trimethobenzamide hydrochloride,) distributed by Monarch Pharmaceuticals, Inc., one page.
Morgan, N. et al. (1999). "Migraine Headaches," University of Wisconsin Hospitals and Clinics Authority, Department of Nursing, UWH #5355, six pages.

(Continued)

Primary Examiner — Sreeni Padmanabhan
Assistant Examiner — Uma Ramachandran
(74) Attorney, Agent, or Firm — Morrison & Foerster LLP

(57) ABSTRACT

Compositions, methods and kits are provided for the treatment of migraines. The compositions, methods and kits include an effective dose of trimethobenzamide and an ethanolamine antihistamine that, when administered to an individual suffering from migraine headaches, will alleviate symptoms associated with the migraine headaches. Compositions, methods, and kits for the treatment of migraines include pharmaceutical compositions of trimethobenzamide and diphenhydramine.

21 Claims, No Drawings

(56) References Cited

OTHER PUBLICATIONS

Nelson, T.P. (2002). "Postoperative Nausea and Vomiting: Understanding the Enigma," Continuing Education Articles Online by American Society of PeriAnesthesia Nurses located at <http://www.aspan.org.EdCe2002Jun.html>, last visited on Apr. 13, 2004, fifteen pages.

Silberstein, S.D. et al. (Feb. 1, 2002). "The State of Migraine: Prevention and Treatment," ACCESS Medical Group, Department of Continuing Medical Education, Arlington Hts.: IL pp. 1-32.

The Robert Wood Johnson Foundation (1999). "Education for Physicians on End-Of-Life Care," Powerpoint Presentation by American Medical Association's Institute for Ethics, pp. 1-45.

Wadibia, E.C. (Feb. 1999). "Antiemetics" Southern Medical Journal 92(2):162-165.

Weisz, M.A. et al. (Jun. 1994). "Home Administration of Intramuscular DHE for the Treatment of Acute Migraine Headache," Headache 34(6):371-373 (Abstract Only).

Yeh, H.-M. et al. (Jul. 2000). "Prophylactic Intravenous Ondansetron Reduces the Incidence of Intrathecal Morphine-Induced Pruritus in Patients Undergoing Cesarean Delivery," Anesthesia and Analgesia 91(1):172-175. (Abstract Only).

* cited by examiner

METHODS FOR TREATMENT OF MIGRAINE AND SYMPTOMS THEREOF

CROSS-REFERENCE TO RELATED APPLICATIONS

This application is a divisional application of U.S. patent application Ser. No. 10/871,847, filed Jun. 17, 2004 (now abandoned), the contents of which are hereby incorporated by reference in their entirety.

STATEMENT REGARDING FEDERALLY SPONSORED RESEARCH OR DEVELOPMENT

Not applicable.

REFERENCE TO A COMPACT DISK APPENDIX

Not applicable.

TECHNICAL FIELD

This invention relates to compositions for the treatment of migraines, and also relates to methods for treatment of migraines. This invention also relates to the compositions and methods for the treatment of symptoms associated with migraines, including headache, nausea, dizziness, etc.

BACKGROUND OF THE INVENTION

Approximately 28 million Americans are estimated to suffer from migraine attacks, the majority of them women (20 million; Lipton et al. 2001 Headache 41(7): 646-657), making this one of the most prevalent disorders today, yet it has been reported that only a minority of sufferers are diagnosed and receive appropriate treatment (Silberstein et al., 2002 "Monograph: The State of Migraine: Prevention and Treatment" ACCESS Medical Group, Department of Continuing Medical Education, 3395 North Arlington Heights Road, Suit A, Arlington Heights, Ill. 600004-1566; Diamond 2001 Postgraduate Medicine 109(1): 49-60: "A fresh look at migraine therapy"; Morgan et al. "Migraine Headaches", 1998, University of Wisconsin Hospitals and Clinics Authority, Madison, Wis., Department of Nursing UWH #5355<www.texaschildneurology.com/migraine %20Headaches.htm>).

Characterization of the Migraine Disorder

The disorder characterized as "migraine" is generally considered a form of headache. However, migraine is a neurological multifactorial syndrome, of which headache is only one of the many ways the disease manifests itself. Migraines are characterized by recurrent attacks of severe, pulsating and disabling headache, vomiting, photo- and phonofobia and malaise, all of which generally worsens with movement. In 20% of the patients additional transient focal neurological (aura) symptoms may occur. The attacks occur in two forms, migraine without aura (common migraine), which occurs in 75% of the patients and with aura (classic migraine), occur in about 30% of the migraineurs. Both types however are experienced in one third of the subjects (<http://en. wikipedia.org/wiki/Migraine>; U.S. Pat. No. 6,465,517).

While it is apparent that migraine and the disability associated with severe migraine symptoms are a public health problem, the exact causes and mechanisms are still widely debated, which hampers treatment and diagnosis of the disorder. However, generic factors might be involved in the disease. It has also been suggested that patients may suffer from a defect in ion channels and have a disturbed energy metabolism in brain and skeletal muscle. These above described features are not observed with ordinary headache such as for example tension headache (U.S. Pat. No. 6,465, 517). Empirical evidence has also suggested links between hormone levels and migraine. Hormonal levels in menstruating women are also implicated in the incidence of migraine.

In addition, certain comorbidities have also been observed in migraine sufferers, where "comorbidity" refers to a greater-than-coincidental association of two or more conditions in the same person. Migraine has been associated with several neurologic and psychological disorders, including epilepsy, depression, anxiety disorders, stroke, bipolar disorder and impaired cognition. Other comorbidities include irritable bowel syndrome, asthma, and mitral valve prolapse (Diamond 2002). Migraine associate with auras seem to be particularly linked to a higher incidence of stroke.

The symptoms and their timing vary considerably among migraine suffers, and to a lesser extent from one migraine attack to the next. Symptoms may vary in severity and regularity of occurrence as well as duration. Migraine can accompany, in some cases, other types of headaches, for example, tension headaches. Migraine often runs in families and can start in adolescence, although some research indicates that it can start in early childhood or even in utero. Silberstein et al., 2002 "Monograph: The State of Migraine: Prevention and Treatment" ACCESS Medical Group, Department of Continuing Medical Education, 3395 North Arlington Heights Road, Suit A, Arlington Heights, Ill. 600004-1566; Diamond 2001 Postgraduate Medicine 109(1): 49-60: "A fresh look at migraine therapy"; Morgan et al. "Migraine Headaches", 1998, University of Wisconsin Hospitals and Clinics Authority, Madison, Wis., Department of Nursing UWH #5355<www.texaschildneurology.com/migraine %20Headaches.htm>; <http://en.wikipedia.org/wiki/Migraine>; U.S. Pat. No. 6,465,517).

Current Treatments

There are numerous regimens of suggested treatment for migraine and the symptoms which are part of the migraine disorder. However, to date, there does not appear to be a single treatment (including prevention or prophylaxis) that is successful for the majority of migraine sufferers. Additionally, treatment that has proven effective in a particular migraine sufferer may not continue to be successful, or may only be intermitently effective. The current standard of care for migraines focuses on three major areas: preventive drugs; avoidance of migraine triggers (e.g., particular foods, alcohol or other substances (e.g., paints, perfumes, etc.), exposure to certain environmental factors, and changes in sleep or lifestyle patterns, etc.); and/or drugs which treat migraine or the symptoms thereof once a migraine has developed (e.g., sumitriptan, analgesics, narcotic medications, antipsychotic drugs, anti-emetics (e.g., compazine). Treatment during migraine is often either ineffective, only partially effective or the therapeutica agents are associated with significant undesirable side effects, including one or more of: hypotension, tiredness, increased weight, breathlessness, dizziness, heaviness or pressure on the chest and arms, shortness of breath, chest pain, nausea, muscle cramps, or peripheral vasoconstriction; depending on the therapy of choice.

Imitrex® (sumitriptan) and related 5-hydroxytryptamine (serotonin) receptor agonists are now available and are often considered the therapy of choice for severe migraine that is relatively infrequent. These serotonin receptor agonists are effective and generally have few side effects when used occasionally. Side effects usually consist of dizziness, heaviness or pressure on the chest and arms, shortness of breath, and sometimes chest pain. Triptans are contra-indicated for patients with coronary artery disease. Some members of this family of drugs are: sumatriptan, zolmitriptan, naratriptan, rizatriptan, elitriptan. (http://en.wikipedia.org/wiki/Migraine>; U.S. Pat. Nos. 6,465,517; 6,255,334; 5,872,145; 5,721,252.)

As described above and known to those of skill in the art, a number of different therapies are available which may prevent or alleviate migraine some of the time for some individuals, but complete avoidance of the disease seems to be impossible and most of the prescribed drugs are known for their undesired side-effects. Certain beta-adrenoreceptor antagonists (propranolol, metoprolol, atenolol) have been described as efficacious for prevention or prophylaxis. However, beta-blockers have multiple side effects, like hypotension, tiredness, increased weight and breathlessness. For a number of years ergotamine or other ergot alkaloids were the only drugs for the treatment of migraine. (See for example U.S. Pat. No. 6,685,951.) However, they have low oral and rectal bioavailablity and may cause nausea, muscle cramps, or peripheral vasoconstriction. Further, calcium channel blockers, hormonal manipulators, analgesics, and non-steroidal anti-inflammatory drugs (NSAID's) are sometimes prescribed, but evidence for preventive efficacy is rare. Numerous patents and references are available detailing the current standard of care for migraine. See for example: U.S. Pat. Nos. 6,479,551; 6,716,837; 6,635,639, 6,476,042; 6,402,678; 6,077,539; 6,380,242, 6,255,334; 6,503,884; 6,251,935; 4,443,464; 5,744,4872; 5,036,078, 5,538,959; U.S. Pat. App. No. 2003/0008892 A1 and references cited therein.

Given the prevalence of the disorder and the related adverse effects on quality of life, productivity and medical costs, migraine has been characterized as a public health crisis (Silberstein et al., 2002, and references cited therein). In the American Migraine Study II (Lipton et al. 2001 *Headache* 41(7): 646-657), results were reported indicating that the highest incidence of migraine in women, the majority of sufferers, occurs between the ages of 25 and 55, the most productive years for the average working adult. Further, an increase in both severity and frequency of attacks was observed for women in their 30s. These statistics, along with the characteristics of migraine as a disorder—painful, debilitating and resulting in the loss of productivity in the workplace and participation with friends and family—highlights the need for effective therapies for a broad range of individuals. To date, there does not appear to be a drug or regimen which can effectively treat a broad range of those suffering from the pain and unpredictability associated with migraine. As is apparent from the studies quoted above, and any of the publicly available materials regarding migraines, e.g., public health (e.g., <www.headaches.org>), university, "self-help" websites, medical journals and continuing medical education monographs, there is an urgent need for effective drugs and treatment regimes to manage this disorder. (Silberstein et al., 2002 *"Monograph: The State of Migraine: Prevention and Treatment"* ACCESS Medical Group, Department of Continuing Medical Education, 3395 North Arlington Heights Road, Suit A, Arlington Heights, Ill. 600004-1566; Diamond 2001 Postgraduate Medicine 109(1): 49-60: "A fresh look at migraine therapy"; Morgan et al. "Migraine Headaches", 1998, University of Wisconsin Hospitals and Clinics Authority, Madison, Wis., Department of Nursing UWH #5355<www.texaschildneurology.com/migraine %20Headaches.htm>; <http://en.wikipedia.org/wiki/Migraine>; U.S. Pat. Nos. 6,465,517; 6,479,551; 6,716,837; 6,635,639, 6,476,042; 6,402,678; 6,077,539; 6,380,242, 6,255,334; 6,503,884; 6,251,935; 4,443,464).

All references, patent, and patent applications cited herein are hereby incorporated by reference in their entirety.

BRIEF SUMMARY OF THE INVENTION

The present invention relates to compositions, methods, and kits for the treatment of migraine headaches. In one embodiment, the invention provides a composition consisting essentially of a therapeutically effective amount of trimethobenzamide and an ethanolamine antihistamine. In certain embodiments, the antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In certain embodiments, the antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In certain embodiments, the antihistamine is doxylamine, diphenhydramine, bromodiphenhydramine, or dimenhydrinate. In certain embodiments, the antihistamine is diphenhydramine. In certain embodiments, the composition is formulated for non-parenteral delivery, such as for oral delivery, or the composition is formulated for parenteral delivery, such as via intra venous delivery or via injection. In certain embodiments, the composition is formulated for injection or oral delivery.

In one embodiment, the invention provides a pharmaceutical composition consisting essentially of a therapeutically effective amount of trimethobenzamide and an ethanolamine antihistamine, wherein the pharmaceutical composition further comprises one or more pharmaceutically acceptable excipients, adjuvants, diluents or stabilizers. In certain embodiments, the antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In certain embodiments, the antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In certain embodiments, the antihistamine is doxylamine, diphenhydramine, bromodiphenhydramine, or dimenhydrinate. In certain embodiments, the antihistamine is diphenhydramine. In certain embodiments, the composition is formulated for non-parenteral delivery, such as for oral delivery, or the composition is formulated for parenteral delivery, such as via intra venous delivery or via injection. In certain embodiments, the composition is formulated for injection or oral delivery.

In one embodiment, the invention provides a composition comprising a therapeutically effective amount of trimethobenzamide and diphenhydramine. In certain embodiments, the composition is formulated for non-parenteral delivery. In certain embodiments, the composition is formulated for oral delivery. In certain embodiments, the composition is formulated for parenteral delivery, such as via intra venous delivery or via injection. In certain embodiments, the composition is formulated for injection.

In one embodiment, the invention provides a pharmaceutical composition comprising a therapeutically effective amount of trimethobenzamide and diphenhydramine, wherein the pharmaceutical composition further comprises one or more pharmaceutically acceptable excipients, adjuvants, diluents or stabilizers. In certain embodiments, the composition is formulated for non-parenteral delivery. In certain embodiments, the composition is formulated for oral delivery. In certain embodiments, the composition is formulated for parenteral delivery, such as via intra venous delivery or via injection. In certain embodiments, the composition is formulated for injection.

In one embodiment, the invention provides a method for the treatment of migraines comprising administering to an individual in need thereof a unit dose of a composition consisting essentially of trimethobenzamide and an ethanolamine antihistamine. In certain embodiments, the method further comprises the administration of an additional unit dose after a period of time, such as after at least one month. In certain embodiments, the method comprises a prophylactic treatment, wherein the unit dose is administered about one time per month. In certain embodiments of the method, the antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In certain embodiments of the method, the antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In certain embodiments of the method, the antihistamine is doxylamine, diphenhydramine, bromodiphenhydramine, or dimenhydrinate. In certain embodiments of the method, the antihistamine is diphenhydramine. In certain embodiments of the method, the composition is formulated for non-parenteral delivery, such as oral delivery. In certain embodiments of the method, the composition is formulated for parenteral delivery, such as via intra venous delivery or via injection. In certain embodiments of the method, the composition is formulated for injection or oral delivery. In certain embodiments of the invention, the composition is a pharmaceutical composition further comprising one or more pharmaceutically acceptable excipients, adjuvants, diluents or stabilizers.

In one embodiment, the invention provides a method for the treatment of migraines comprising administering to an individual in need thereof a unit dose of a composition comprising trimethobenzamide and diphenhydramine. In certain embodiments, the method further comprises the administration of an additional unit dose after a period of time, such as after at least one month. In certain embodiments, the method comprises a prophylactic treatment, wherein the unit dose is administered about one time per month. In certain embodiments of the method, the composition is formulated for non-parenteral delivery. In certain embodiments of the method, the composition is formulated for oral delivery. In certain embodiments of the method, the composition is formulated for parenteral delivery, such as via intra venous delivery or via injection. In certain embodiments of the method, the composition is formulated for injection. In certain embodiments of the method, the composition is a pharmaceutical composition further comprising one or more pharmaceutically acceptable excipients, adjuvants, diluents or stabilizers.

In one embodiment, the invention provides a kit for the treatment of migraines comprising a pharmaceutical composition consisting essentially of a unit dose of trimethobenzamide and an ethanolamine antihistamine, wherein the pharmaceutical composition further comprises one or more pharmaceutically acceptable excipients, adjuvants, diluents or stabilizers. In certain embodiments, the kit further comprises instructions for use. In certain embodiments of the kit, the pharmaceutical composition is formulated for parenteral delivery. In certain embodiments of the kit, the pharmaceutical composition is formulated for injection and the kit further comprises a syringe.

In certain embodiments of the kit, the pharmaceutical composition is formulated for intra venous delivery. In certain embodiments of the kit, the pharmaceutical composition is formulated for non-parenteral delivery, such as for oral delivery. In certain embodiments of the kit, the unit dose of trimethobenzamide and an ethanolamine antihistamine may be formulated as a mixture or may be provided in separate dosage forms, and wherein the kit may comprise one or more unit doses. In certain embodiments of the kit, the unit dose of trimethobenzamide and an ethanolamine antihistamine is formulated as a mixture.

In one embodiment, the invention provides a kit for the treatment of migraines comprising a pharmaceutical composition comprising a unit dose of trimethobenzamide and diphenhydramine, wherein the pharmaceutical composition further comprises one or more pharmaceutically acceptable excipients, adjuvants, diluents or stabilizers. In certain embodiments, the kit further comprises instructions for use. In certain embodiments of the kit, the pharmaceutical composition is formulated for parenteral delivery. In certain embodiments of the kit, the pharmaceutical composition is formulated for injection and the kit further comprises a syringe. In certain embodiments of the kit, the pharmaceutical composition is formulated for intra venous delivery.

In certain embodiments of the kit, the pharmaceutical composition is formulated for non-parenteral delivery, such as for oral delivery. In certain embodiments of the kit, the unit dose of trimethobenzamide and diphenhydramine may be formulated as a mixture or may be provided in separate dosage forms, and wherein the kit may comprise one or more unit doses. In certain embodiments of the kit, the unit dose of trimethobenzamide and diphenhydramine is formulated as a mixture.

DETAILED DESCRIPTION OF THE INVENTION

Provided herein are compositions and methods for the treatment of migraine which are broadly and consistently effective in relieving symptoms during a migraine attack and preventing recurrence in habitual, longterm migraneurs. As described herein, co-administration of trimethobenzamide and an ethanolamine antihistamine, including the compositions described herein, is therapeutically effective in reducing or eliminating the symptoms of migraine within a short period of time following administration and a single dosing is often effective for weeks, months or longer in preventing the recurrence of migraine. In particular embodiments of the invention are provided compositions comprising trimethobenzamide and diphenhydramine and methods of use for treating migraine therewith.

Migraine Treatment

As described above, "migraine" is a term used to describe a multifactorial disorder whose exact cause is unknown and which, to date, there has been little success in developing effective therapeutics which are consistently efficacious for a wide range of individuals in need thereof.

As used herein, the term "migraine" refers to all classifications of migraines, and treatment of this disorder refers to the treatment of the headache and/or other associated symptoms of the disorder, including, but not limited to both "classical" (with aura) and other migraines. These include all types of migraines, including those referred to as menstrual migraines, cluster headaches, hemiplegic migraines, basilar migraines, etc. The compositions and methods described herein may also be used in the treatment of pediatric migraine.

Additionally the compositions and their uses as described herein are not limited by the triggering event which may proceed a migraine. Examples of triggering events include, but are not limited to, particular environmental factors (e.g., light, glare, noise, odors (including perfume or other volatile compounds or mixtures thereof (e.g., paint, household or industrial cleaners, deodorizers, etc.), altitude changes, weather changes, weather conditions, insecticides, second hand smoke, flickering light (e.g., fluorescent, computer or video monitors, etc)), "allergic" or other reactions to substances (e.g., foods (e.g., chocolate, cheese, nuts, coffee, preserved meats, tomatoes, citrus fruits, etc.), alcohol (e.g., red wine, spirits, etc.), chemicals (e.g., sulfites, etc.)), sweeteners (e.g., aspartame, etc.) preservatives, flavor enhancers (e.g., MSG, etc.) drug interactions, etc.) or physiological factors.

Physiological factors which may act as migraine triggers include, but are not limited to, stress, exercise, hormonal changes, birth control pills, too much or too little sleep, or a change in sleep pattern, medicines (e.g., antibiotics (such as, tetracycline, griseofulvin, etc.), antihypertensives (such as, nifedipine, captopril, etc.), hormones (such as, oral contraceptives, estrogens, etc.), histamine-2 blockers (such as, cimetidine, ranitidine, etc.), vasodilators (such as, nitroglycerin, isosorbide dinitrate, etc.) antihistamines (e.g., anticholinergics, aspirin or diuretics), hypoglycemia and missing meals. Migraines may also be triggered by any other type of headache. The methods and compositions herein are not intended for use in the treatment of headaches or earaches associated with sinusitis or earaches not associated with migraine.

The compositions and uses thereof described herein are intended to treat migraine at any stage, including, but not limited to, before occurrence (prevention, prophylaxis), after experience of a triggering event but prior to occurrence of headache, concomitant with or after the occurrence of a signalling symptom associated with impending migraine (e.g., an aura) and during the migraine attack.

The term "treatment" as used herein, and as well understood in the art, is an approach for obtaining beneficial or desired results, including clinical results. For purposes of this invention, beneficial or desired clinical results can include one or more, but are not limited to, alleviation or amelioration of one or more symptoms, diminishment of extent of the disorder, stabilized (i.e., not worsening) state of disorder, including amelioration or palliation of the symptoms of the disorder, and prevention or diminishment (whether partial or total) of occurrences of migraine attacks. For each of the foregoing, the amelioration or alleviation may pertain to a lessening in one or more of the frequency, severity, duration or number of symptoms experienced by an individual who suffers from migraines.

Migraine attacks are known to last from hours to days. It has been reported that the typical migraine may last from hours to up to 3 or 4 days. The actual migraine "attack" can be considered to be that period during which the migraneur may be suffering the pain associated with a migraine headache or any of the other symptoms associated with a migraine (with or without concomitantly experiencing the headache). The administration of the compositions described herein may be at any point during the migraine attack, or may be prior to the onset of the migraine attack, but after experiencing a known or suspected triggering event (e.g., exposure to known or suspected environmental factor, chemical, during particular portions of the menstrual cycle, changes in altitude, weather, etc.). The administration of the compositions described herein may be prophylactic, i.e. prior to onset of migraine or experiencing a known triggering event, and taken routinely, such as monthly, to prevent recurring migraine attacks.

Symptoms associated with the migraine disorder and experienced during some portion of the migraine attack may include, but are not limited to, one or more of headache, naseau, aura (e.g., visual changes such as bright flashing lights; flickering, colored zigzag lines; blind spots; loss of vision off to one side, a tingling sensation or numbness in the arms or legs, dizziness, etc.), photophobia, phonophobia, or vomiting. Other symptoms experienced may also include abdominal pain, particularly in children.

Compositions

Trimethobenzamide

Trimethobenzamide (also referred to as "trimethoxybenazamide") belongs to the class of anti-emetics known as "substituted benzamides." The classification is based on the similarity of the basic chemical structure. Other substituted benzamides include metoclopramide, cisapride, sulpiride, tiapride, and sultopride. However, while most substituted benzamides have anti-emetic activity, the pharmacological profile, including side effects and indication for use, across this structurally related family differs significantly. For instance, cisapride was found to be ineffective for migraine prevention, while Metoclopramide exerted an antimigraine effect (Fanciullacci et al., "Dopamine involvement in the migraine attack", Funct Neurol. 2000; 15 Suppl 3:171-81, Dept. of Internal Medicine, Headache Center, University of Florence, Italy). Trimethobenzamide is further classified as an anti-cholinergic therapeutic.

Trimethoxybenzamide is shown below in its hydrochloride salt form, also referred to as N-[p-[2-(dimethylamino)ethoxy]benzyl]-3,4,5-trimethoxybenzamide monohydrochloride. It is a commercially available pharmaceutical known as Tigan®. Tigan® is generally administered via injection for treatment of uncontrollable vomiting. When administered alone, adverse reactions may include hypersensitivity, Parkinson-like symptoms, hypotension, blood dyscrasias, diskinesia, blurring of vision, coma, convulsions, depression, diarrhea, disorientation, dizziness, drowsiness, headache, jaundice, muscle cramps, and opisthotonos. Use of Tigan® is contraindicated in children and individuals with known hypersensitivity to trimethobenzamide. As used herein, the term "trimethoxybenzamide" is taken to refer to the compound as shown below, including free acid or any salt forms, solvates, or steroisomers thereof, including mixtures of the foregoing.

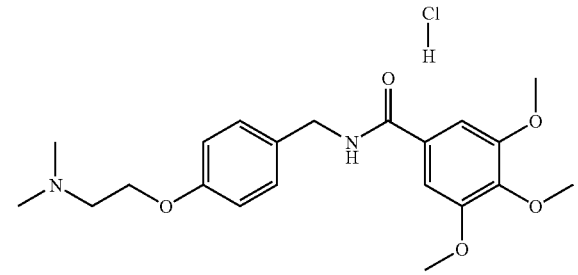

Antihistamines

Antihistamines are compounds (drugs) which block the action of histamine, and thus prevent or alleviate symptoms of an allergic response. Most antihistamines selectively bind to, but do not activate, either the H1 or H2 histamine receptors, or a combination of both receptors. Compounds which bind to, but do not activate the histamine receptors are also referred to as blocking or antagonizing the histamine receptor, or, as histamine antagonists or histamine inhibitors.

Some antihistamines are selective for either the H1 or H2 receptor. Antihistamines generally referred to as "classical antihistamines" are generally attributed to block the H1 receptor. H1 receptor antagonists block the H1 receptors in, for example, bronchi, capillaries and certain other smooth muscles, and are used to prevent or allay, for example, motion sickness, seasonal rhinitis, allergic dermitis and, sometimes to induce somnolence. Some H1 antihistamines also block H1 receptors of the central nervous system and are not as well understood.

Antihistamines are also broadly classed as central nervous system (CNS) depressants, and certain antihistamines are differentiated based upon their CNS side effect of being either sedating (e.g., most H1 antagonists, chlopheniramine, etc.) or non-sedating (e.g., loratadine).

Antihistamines are also classified according to the chemical structure. For examples, classes of antihistamines include piperazines (e.g., compazine, meclozine, hydroxyzine, etc.); piperadines (e.g., azatadine, triprolidine, etc.); phenothiazines (e.g., thorazine, temaril, etc.); tricyclic antidepressants (e.g., imipramine, doxopin, amitryptoline, etc.); ethylenediamines (e.g., PBZ, etc.); alkylamines (e.g., brompheniramine, chlorpheniramine, etc.); and others (e.g., terfenadine, astemizole, loratadine, acrivastine, etc.). Ethanolamine antihistamines are another class of antihistamines.

Ethanolamine Antihistamines

The ethanolamine antihistamines include, for example, doxylamine (3475, N,N-Dimethyl-2-[1-phenyl-1-(2-pyridinyl)ethoxy]ethanamine (Merck), Dimethyl-[2-(1-phenyl-1-pyridin-2-yl-ethoxy)-ethyl]-amine (Autonom)), diphenhydramine (3341, 2-Diphenylmethoxy-N,N-dimethylethanamine (Merck) (2-Benzhydryloxy-ethyl)-dimethyl-amine (Autonom)), bromodiphenhydramine (1402, 2-[(4-Bromophenyl)phenylmethoxy]-N,N-dimethylethaneamine (Merck), {2-[(4-Bromo-phenyl)-phenyl-methoxy]-ethyl}-dimethyl-amine (Autonom)), dimenhydrinate (3231, 2-(benzhydryloxy)-N,N-dimethylethylamine 8-chlorotheophyllinate or diphenhydramine 8-chlorotheophyllinate (Merck)), bietanautine (1210, 2-(benzhydryloxy)-N,N-dimethylethylamine bis(theophylline 7-acetate) (Merck)), carbinoxamine (1808, 2-[(4-Chlorophenyl)-2-pyridinylmethoxy]-N,N-dimethylethanamine (Merck), {2-[(4-Chloro-phenyl)-pyridin-2-yl-methoxy]-ethyl}-dimethyl-amine (Autonom)), embramine (3588, 2-[1-(4-Bromophenyl)-1-phenylethoxy]-N,N-dimethylethanamine (Merck), {2-[1-(4-Bromo-phenyl)-1-phenyl-ethoxy]-ethyl}-dimethyl-amine (Autonom)), medrylamine, moxastine (6312, 2-(1,1-Diphenylethoxy)-N,N-dimethylethanamine (Merck), [2-(1,1-Diphenyl-ethoxy)-ethyl]-dimethyl-amine (Autonom)), p-methyldiphenhydramine (6078, N,N-Dimethyl-2-[(4-methylphenyl)phenylmethoxy]ethanamine (Merck), Dimethyl-[2-(phenyl-p-tolyl-methoxy)-ethyl]-amine (Autonom)), orphenadrine (6945, N,N-Dimethyl-2-[(2-methylphenyl)phenylmethoxy]ethanamine (Merck), Dimethyl-[2-(phenyl-o-tolyl-methoxy)-ethyl]-amine (Autonom)), phenyltoloxamine (7400, N,N-Dimethyl-2-[2-phenylmethyl)phenoxy]ethanamine (Merck), [2-(2-Benzyl-phenoxy)-ethyl]-dimethyl-amine (Autonom)), and setastine (8548, 1-[2-[1-(4-Chlorophenyl)-1-phenylethoxy]ethyl]hexahydro-1H-azepine (Merck), 1-{2-[1-(4-Chloro-phenyl)-1-phenyl-ethoxy]-ethyl}-azepane (Autonom)). Clemastine (2367, (2R)-2-[2-[(1R)-1-(4-Chlorophenyl)-1-phenylethoxy]ethyl]-1-methylpyrrolidine (Merck)) and diphenylpyraline (3363, 4-(Diphenylmethoxy)-1-methylpiperidine (Merck), 4-Benzhydryloxy-1-methyl-piperidine (Autonom)), are closely related in activity to these ethanolamine antihistamines, and while they are not strictly ethanolamines, are included in this class of antihistamines. The numbers after each compound indicate the monograph number from the thirteenth edition of the Merck Index. The names are either from Autonom version 2.1 (Beilstein Informationssysteme GmbH) module in ChemDraw Ultra version 6.0.2 (CambridgeSoft.com, Cambridge, Mass.), or the Merck Index. Most of these ethanolamine antihistamines are commercially available pharmaceutical compositons, for example diphenydramine is available as Benadryl®, dimenhydrinate is available as Dramamine®.

Like certain other antihistamines, many ethanolamine antihistamines are known to also possess anticholinergic effects which may contribute to drug interactions and/or side effects. For example, possible side effects of diphenhydramine include hypotension, headache, palpitations, tachycardia, extrasystoles, sedation, sleepiness, dizziness, epigastric distress, and diarrhea. It is contraindicated for use in neonates, premature infants, and nursing mothers. Diphenhydramine may also be administered to individuals who have adverse diskinesia side effects following treatment with trimethobenzamide for uncontrolled vomiting (occurs in approximately <2% of individuals treated). The co-administration of diphenhydramine for treatment of migraine does not appear to have been previously known. The structures of exemplary ethanolamine antihistamines are shown below, and include any salt forms, solvates, or stereoisomers thereof.

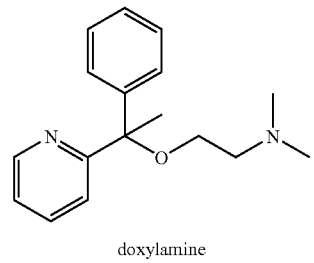

doxylamine

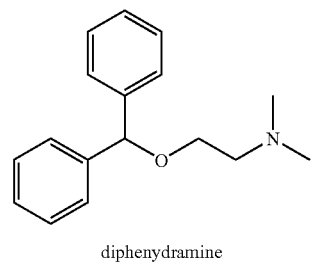

diphenydramine

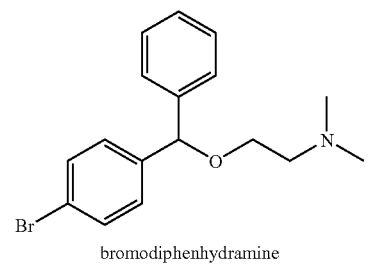

bromodiphenhydramine

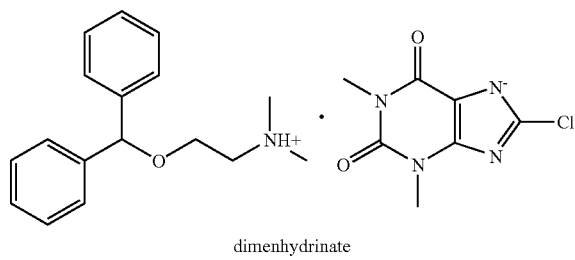

dimenhydrinate

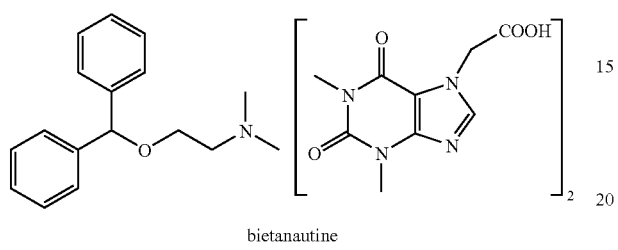

bietanautine

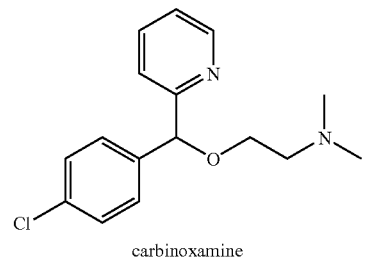

carbinoxamine

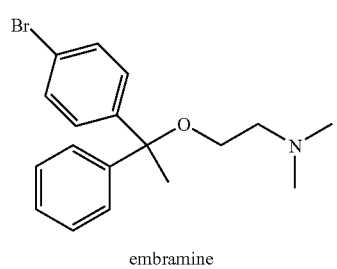

embramine

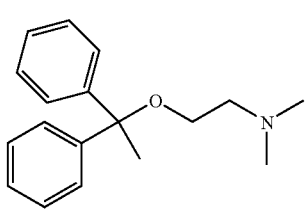

moxastine

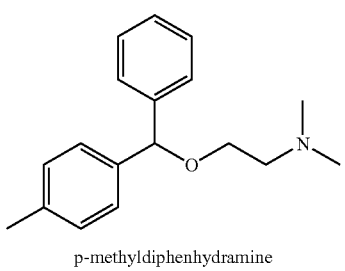

p-methyldiphenhydramine

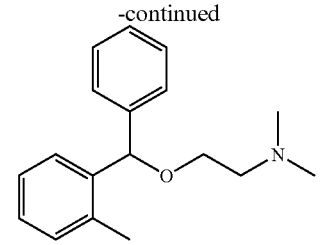

orphenadrine

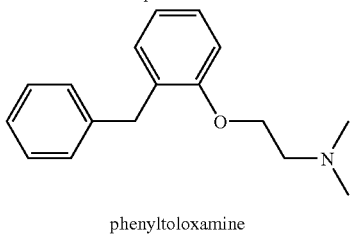

phenyltoloxamine

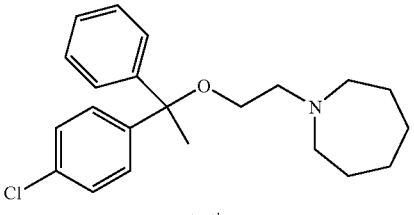

setastine

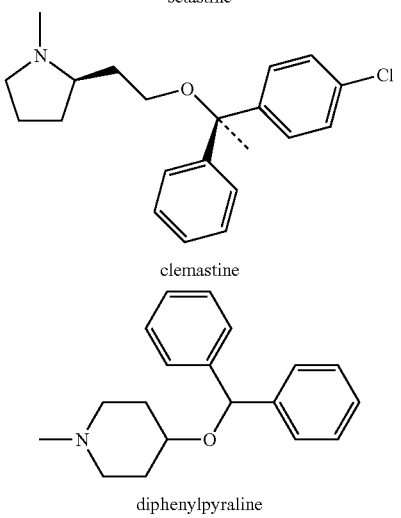

clemastine diphenylpyraline

Anti-Migraine Compositions

The present invention encompasses compositions consisting essentially of a therapeutically effective amount of a substituted benzamide antiemetic and an ethanolamine antihistamine. A therapeutically effective amount is one that provides effective treatment of migraines. For example, upon administration of a therapeutically effective amount to an individual suffering from migraines, the symptoms disappear within less than about 1 hour, less than about 30 minutes, less than about 20 minutes, less than about 15 minutes, less than about 10 minutes, or less than about 5 minutes following the administration of the therapeutically effective amount.

In one embodiment of the invention, the substituted benzamide antiemetic is trimethobenzamide and the ethanolamine antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In another embodiment of the invention, the substituted benzamide antiemetic is trimethobenzamide and the ethanolamine antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In another embodiment of the invention, the substituted benzamide antiemetic is trimethobenzamide and the ethanolamine antihistamine is doxylamine, diphenhydramine, bromodiphenhydramine, or dimenhydrinate. In another embodiment of the invention, the compositions consist essentially of a therapeutically effective amount of trimethobenzamide and diphenhydramine.

The invention also encompasses a composition comprising a therapeutically effective amount of trimethobenzamide and diphenhydramine, including any salt forms, solvates, or steroisomers thereof.

All compositions discussed herein encompass pharmaceutical compositions of the two compounds, whether formulated separately or as a mixture. For example, a pharmaceutical composition of trimethobenzamide and diphenhydramine would include separate formulations, e.g. separate capsules, tablets, gels, etc. for oral delivery or separate solutions for parenteral delivery, such as separate vials for injection. A pharmaceutical composition, for example, of trimethobenzamide and diphenhydramine would also include a mixture of the two in the same formulation, e.g. in one capsule, tablet, gel, etc. for oral delivery or one solution for parenteral delivery, such as one vial for injection. A mixture of the compounds is any pharmaceutical composition comprising an effective amount of the compounds, wherein the compounds may be mixed at any point in the process of making the compounds and formulating the pharmaceutical composition.

In another aspect of the invention, the therapeutically active anti-migraine composition, and methods of using the composition, encompass where the moieties of the trimethobenzamide and ethanolamine antihistamine are combined in a single therapeutically active anti-migraine compound.

Such therapeutically active compounds include where the trimethobenzamide and ethanolamine antihistamine are linked via a frangible linker or a non-frangible linker, as known to those of skill in the art. In certain embodiments, the anti-migraine compound comprises the trimethobenzamide and diphenhydramine moieties. The moieties so incorporated into the anti-migraine compound may include the entire trimethobenzamide or ethanolamine antihistamine molecule (absent atoms as necessary at the linking site), or the portion of the trimethobenzamide or ethanolamine antihistamine necessary for therapeutic activity.

Methods of Migraine Treatment

Migraines are effectively treated by the co-administration of trimethobenzamide and an ethanolamine antihistamine. A therapeutically effective amount of trimethobenzamide and an ethanolamine antihistamine may be co-administered via parenteral or non-parenteral delivery. Co-administration is defined as administration of the therapeutically effective amount of each compound simultaneously, or within a certain period of time. For example, the compounds may be formulated as a mixture that is administered, as separate formulations administered simultaneously, or as separate formulations administered within a time period, such as within less than about 1, 2, 3, 4, 5, 6, 7, 8, 9, 10, 15, 20 or 30 minutes of each other, wherein either compound can be administered first.

The compounds can be formulated for parenteral delivery, such as intra venous (IV), intra muscular (IM) injection, or intra peritoneal (IP) injection, or for non-parenteral delivery, such as oral (e.g. tablet, capsule, gel, etc.), topical (e.g., transdermal, etc.), nasal, inhaler, or suppository. The term "injection" can refer to both IM and IP delivery. When administered separately, the trimethobenzamide can be formulated for parenteral delivery or non-parenteral delivery and the ethanolamine antihistamine can be formulated independently for parenteral delivery or non-parenteral delivery. Any combination of delivery of a therapeutically effective amount may be co-administered, such as parenteral delivery of both compounds, non-parenteral delivery of both compounds, parenteral delivery of trimethobenzamide with non-parenteral delivery of the ethanolamine antihistamine, or non-parenteral delivery of trimethobenzamide with parenteral delivery of the ethanolamine antihistamine. In certain embodiments, the therapeutically effective amounts of trimethobenzamide and the ethanolamine antihistamine are formulated as a mixture for parenteral (e.g., injection, etc.) or non-parenteral (e.g., oral, etc.) delivery. In particular embodiments the trimethobenzamide and ethanolamine antihistamine are administered orally, either with a single tablet or capsule, or simultaneously with separate tablets or capsules. In other embodiments, the trimethobenzamide and ethanolamine antihistamine are administered via injection (e.g., IM, IP), ether as a mixture or via separate injections.

In certain embodiments of the above described methods, the ethanolamine antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In certain embodiments of the above described methods, the ethanolamine antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In certain embodiments of the above described methods, the ethanolamine antihistamine is doxylamine, diphenhydramine, bromodiphenhydramine, or dimenhydrinate. In certain embodiments of the above described methods, the ethanolamine antihistamine is diphenhydramine.

The therapeutically effective amount of trimethobenzamide is one that, in combination with a therapeutically effective amount of an ethanolamine antihistamine, provides effective treatment of migraines, for example where upon administration to an individual suffering from migraines, the symptoms disappear within less than about 1 hour, less than about 30 minutes, less than about 20 minutes, less than about 15 minutes, less than about 10 minutes, or less than about 5 minutes after the administration of the therapeutically effective amount. Similarly, the therapeutically effective amount of an ethanolamine antihistamine is one that, in combination with a therapeutically effective amount of trimethobenzamide, provides effective treatment of migraines, for example where upon administration to an individual suffering from migraines, the symptoms disappear within less than about 1 hour, less than about 30 minutes, less than about 20 minutes, less than about 15 minutes, less than about 10 minutes, or less than about 5 minutes after the administration of the therapeutically effective amount.

A unit dose for the treatment of migraines is the combined therapeutically effective amounts of trimethobenzamide and an ethanolamine antihistamine, whether formulated as a mixture or separately. When a therapeutically effective amount of trimethobenzamide and an ethanolamine antihistamine is formulated as a mixture, the therapeutically effective amount of the mixture is a unit dose of the composition comprising trimethobenzamide and an ethanolamine antihistamine. When the unit dose is not a formulated mixture of the trimethobenzamide and the ethanolamine antihistamine, i.e. when the therapeutically effective amounts of trimethobenzamide and an ethanolamine antihistamine are formulated and administered independently (including simultaneously), a unit dose is the therapeutically effective amounts of each compound co-administered (simultaneously or within a certain time period of each other). When co-administration is not simultaneous, the symptoms disappear within less than about 1 hour, less than about 30 minutes, less than about 20 minutes, less than about 15 minutes, less than about 10 minutes, or less than about 5 minutes after the administration of the last compound administered.

In one embodiment, the method for treatment of migraines comprises co-administering to an individual in need thereof a unit dose of trimethobenzamide and an ethanolamine antihistamine, or administering a unit dose of a composition consisting essentially of trimethobenzamide and an ethanolamine antihistamine. The method may further comprise co-administering one or more additional unit doses of trimethobenzamide and an ethanolamine antihistamine, or administering one or more additional unit doses of a composition consisting essentially of trimethobenzamide and an ethanolamine antihistamine, after a period of time from the initial dose, such as after at least a month. The method of treatment may be prophylactic, wherein an individual who suffers from recurring migraines may be administered unit doses of trimethobenzamide and an ethanolamine antihistamine, or unit doses of a composition consisting essentially of trimethobenzamide and an ethanolamine antihistamine routinely, for example about once a month.

In certain embodiments of the methods described herein, the ethanolamine antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In certain embodiments of the methods described herein, the ethanolamine antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In certain embodiments of the methods described herein, the ethanolamine antihistamine is doxylamine, diphenhydramine, bromodiphenhydramine, or dimenhydrinate. In certain embodiments of the methods described herein, the ethanolamine antihistamine is diphenhydramine.

The methods described herein are for the treatment of migraines specifically, and are not intended to treat non-migraine headaches. Non-migraine headaches include tension (i.e. stress) headaches and secondary headaches, i.e. headaches that are caused by other conditions, such as sinusitis, tooth ache, ear infections, etc. For example, compositions and methods described herein have been used on individuals suffering from sinusitis or ear infections with no effect on the pain associated with these conditions. While not limiting the compositions or methods of the invention to any particular mechanism, it is possible that the combination of trimethobenzamide and ethanolamine antihistamine acts to block the sympathetic nerve, which alleviates migraine headaches and all symptoms associated with migraines.

Kits

The invention also provides kits for the treatment of migraines comprising a pharmaceutical composition consisting essentially of at least one unit dose of a substituted benzamide antiemetic and an ethanolamine antihistamine, wherein the pharmaceutical composition further comprises acceptable excipients, adjuvants, diluents, or stabilizers, wherein a kit includes instructions for use in the treatment of migraines. The unit dose of the substituted benzamide antiemetic and the ethanolamine antihistamine may be formulated separately or as a mixture. These can be formulated with suitable excipients, adjuvants, diluents or stabilizers for either parenteral (e.g. IV, injection (IM or IP)) or non-parenteral (e.g., oral, topical, nasal, inhaler, or suppository) delivery. For example, a unit dose may comprise a formulated mixture of the substituted benzamide antiemetic and the ethanolamine antihistamine. Alternatively, the unit dose may comprise the substituted benzamide antiemetic formulation separate from the ethanolamine antihistamine formulation.

The co-administration of these formulations in accordance with the instructions for use provides the desired therapeutic treatment of migraines. When the unit dose consists essentially of separate formulations, these may be independently formulated for parenteral or non-parenteral delivery. For example, the substituted benzamide antiemetic may be formulated for parenteral delivery while the ethanolamine antihistamine may be formulated for non-parenteral delivery. For ease of administration, both compounds may be formulated for the same type of delivery, including where the substituted benzamide antiemetic and the ethanolamine antihistamine are formulated as a mixture.

In one embodiment of the invention, the substituted benzamide antiemetic and the ethanolamine antihistamine are formulated for parenteral delivery, in some cases as a mixture. In such embodiments, the kit further comprises at least one syringe for delivery of the dose. The formulation for parenteral delivery may comprise a multi-dose formulation, wherein a new syringe is used to remove a unit dose from the multi-dose formulation. In one embodiment, the substituted benzamide antiemetic and the ethanolamine antihistamine are formulated for non-parenteral delivery, such as oral delivery. In certain embodiments, a unit dose is formulated as a mixture of the substituted benzamide antiemetic and the ethanolamine antihistamine for oral delivery, such as a capsule or pill.

In certain embodiments, the substituted benzamide antiemetic is trimethobenzamide and the ethanolamine antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In another embodiment, the substituted benzamide antiemetic is trimethobenzamide and the ethanolamine antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In another embodiment, the substituted benzamide antiemetic is trimethobenzamide and the ethanolamine antihistamine is doxylamine, diphenhydramine, bromodiphenhydramine, or dimenhydrinate. In certain embodiments, the substituted benzamide antiemetic is trimethobenzamide and the ethanolamine antihistamine is diphenhydramine.

In another embodiment, the invention provides kits for the treatment of migraines comprising a pharmaceutical composition consisting essentially of at least one unit dose of trimethobenzamide and an ethanolamine antihistamine, wherein the pharmaceutical composition further comprises acceptable excipients, adjuvants, diluents, or stabilizers, and wherein the kit includes instructions for use for treatment of migraine. The unit dose of the trimethobenzamide and the ethanolamine antihistamine may be formulated separately or as a mixture. These can be formulated with suitable excipients, adjuvants, diluents or stabilizers for either parenteral (e.g., IV, injection (IM or IP)) or non-parenteral (e.g., oral, topical, nasal, inhaler, or suppository) delivery. In another embodiment, the ethanolamine antihistamine is doxylamine, diphenhydramine, bromodiphenhydramine, dimenhydrinate, clemastine, bietanautine, carbinoxamine, diphenylpyraline, embramine, medrylamine, moxastine, p-methyldiphenhydramine, orphenadrine, phenyltoloxamine, or setastine. In another embodiment, the ethanolamine antihistamine is doxylamine, diphenhydramine, bromodiphenhydramine, dimenhydrinate, bietanautine, carbinoxamine, embramine, medrylamine, moxastine, p-methyldiphenhydramine, orphenadrine, phenyltoloxamine, or setastine. In another embodiment, the ethanolamine antihistamine is doxylamine, diphenhydramine, bromodiphenhydramine, or dimenhydrinate. In certain embodiments, the ethanolamine antihistamine is diphenhydramine.

In certain embodiments, the invention provides kits for the treatment of migraines comprising a pharmaceutical composition comprising at least one unit dose of trimethobenzamide and diphenhydramine, wherein the pharmaceutical composition further comprises acceptable excipients, adjuvants, diluents, or stabilizers, wherein a kit includes instructions for use for the treatment of migraines. The unit dose of trimethobenzamide and diphenhydramine may be formulated separately or as a mixture. These can be formulated with suitable excipients, adjuvants, diluents or stabilizers for either parenteral (e.g., IV, injection (IM or IP)) or non-parenteral (e.g., oral, topical, nasal, inhaler, or suppository) delivery.

The unit dose may comprise a formulated mixture of trimethobenzamide and diphenhydramine. Alternatively, the unit dose may comprise a trimethobenzamide formulation separate from a diphenhydramine formulation. The co-administration of these formulations provides the desired therapeutic treatment of migraines (i.e. unit dose). When the unit dose comprises separate formulations, these may be independently formulated for parenteral or non-parenteral delivery. For example, the trimethobenzamide may be formulated for parenteral delivery while the diphenhydramine may be formulated for non-parenteral delivery. For ease of administration, both compounds may be formulated for the same type of delivery, where the trimethobenzamide and the diphenhydramine may be formulated as a mixture.

In one embodiment of the invention, the trimethobenzamide and the diphenhydramine are formulated for parenteral delivery, and may be formulated as a mixture. In such embodiments, the kit may further comprise at least one syringe for delivery of a unit dose. In certain embodiments, the mixture is formulated for IM delivery. The formulation for parenteral delivery may comprise a multi-dose formulation, wherein a new syringe is used to remove a unit dose from the multi-dose formulation. In one embodiment, the trimethobenzamide and the diphenhydramine are formulated for non-parenteral delivery, such as oral delivery. In certain embodiments, a unit dose is formulated as a mixture of trimethoxybenzamide and diphenhydramine for oral delivery, such as a capsule, gel or tablet.

Formulations and Dosage

The compositions discussed herein can be generally administered as pharmaceutical compositions, wherein the pharmaceutical compositions are formulated by methods well know to those skilled in the art. The pharmaceutical compositions are manufacture with acceptable excipients, adjuvants, diluents or stabilizers to provide the appropriate formulation for the desired administration, such as parenteral (e.g., IV, injection (IM or IP)) or non-parenteral (e.g., oral, topical, nasal, inhaler or suppository). As the compounds used in the methods and compositions discussed herein are generally commercially available, the suitable formulations are readily known to those skilled in the art. For example, the compositions and methods discussed herein comprising trimethobenzamide and diphenhydramine were prepared from commercially available pharmaceutical compositions. A commercially available composition of trimethobenzamide for oral delivery, such as a capsule, may contain 250 mg to 300 mg of trimethobenzamide hydrochloride as well as inactive ingredients such as D&C Red No. 28, FD&C Blue No. 1, lactose, magnesium stearate, starch, and titanium oxide. A commercially available composition of trimethoxybenzamide in single dose ampules for injection may contain 200 mg trimethobenzamide hydrochloride in 2 mL, along with inactive ingredients such as 0.2% methyl and propyl parabens (preservatives), 1 mg sodium citrate and 0.4 mg citric acid as buffers, pH adjusted to approximately 5.0 with sodium hydroxide. Similarly, multi-dose vials for injection may contain 100 mg/mL trimethobenzamide hydrochloride, along with inactive ingredients such as 0.45% phenol (preservative) 0.5 mg/mL sodium citrate and 0.2 mg/mL citric acid as buffers, pH adjusted to approximately 5.0 with sodium hydroxide. Similarly, diphenhydramine is commercially available as a composition for injection containing 50 mg/mL diphenhydramine hydrochloride, adjusted to pH 5.0 or 6.0 with either sodium hydroxide or hydrochloric acid, where multi-dose vials may contain additional inactive ingredients, such as 0.1 mg/mL benzethonium chloride as a germicidal agent. Capsules are also commercially available, typically containing 25 mg or 50 mg of diphenhydramine hydrochloride.

While the trimethobenzamide and ethanolamine antihistamines discussed herein are generally commercially available, such that appropriate doses can be readily prepared from existing pharmaceutical compositions, the compositions, methods and kits discussed herein encompass any suitable pharmaceutical formulation of the desired dose of compounds, either formulated as a mixture or separately. Such formulations are known to those skilled in the art, and examples of suitable excipients, adjuvants, diluents or stabilizers can be found, for example, in Gennaro, ed., Remington's The Science and Practice of Pharmacy, $20^{th}$ edition, Lippincott Williams &Wilkins.

The unit dose required for the compositions, methods and kits discussed herein can be adjusted as necessary to suit the individual being treated, for example adjusted to the weight, age or general health of the individual, as is within the skill of a medical practitioner. For a unit dose of trimethobenzamide and an ethanolamine antihistamine such as diphenhydramine, dosage formulated for either parenteral or non-parenteral delivery as discussed herein, comprises trimethobenzamide in the range of approximately 10 mg to 1000 mg, also approximately 25 mg to 500 mg, also approximately 50 mg to 500 mg, also approximately 250 mg to 300 mg and diphenhydramine in the range of approximately 1 mg to 200 mg, also approximately 5 mg to 150 mg, also approximately 10 mg to 100 mg, also approximately 25 to 50 mg. In certain embodiments, the dose is formulated for oral delivery to an adult with 250 mg of trimethobenzamide and 25 mg diphenhydramine. In certain embodiments, an adult dose is formulated for injection with 200 mg trimethobenzamide and 50 mg diphenhydramine in 3 mL solution for injection. Trimethobenzamide is contraindicated in children under 7 years of age via injection or oral delivery. Children under 7 years of age may be treated instead with a 100 mg suppository via the rectum, administered with the ethanolamine antihistamine according to the methods described herein. For the ethanolamine antihistamines, pediatric dosages are calculated according to the known dosing regimens according to the weight and age of the individual for the particular antihistamine. For example, the diphenhydramine pediatric dose for the claimed mixtures is 5 mg/kg/24 hours, where the dose is delivered over 24 hours in 3-4 doses.

The invention discussed herein further encompasses methods of manufacturing a medicament for the treatment of migraine headaches. The methods of manufacturing such medicaments are well known to those skilled in the art. Such medicaments are embodied by the compositions, methods and kits discussed herein.

The invention is further illustrated by the following non-limiting examples.

EXAMPLES

Example 1

Treatment of Migraine Headache with a Single Injection of Trimethobenzamide and Diphenhydramine Individuals with a history of recurrent migraine headaches were selected for treatment. The individuals were queried to assess the symptoms relating to the migraine headaches. These symptoms include pulsating or throbbing headache, photophobia or visual disturbances (e.g. bright flashing lights; flickering, colored zigzag lines; blind spots; loss of vision off to one side), earache or noise disturbances (e.g. phonophobia; buzzing or ringing in ears), nausea or vomiting, abdominal discomfort, limpness or numbness in extremities, tingling (e.g. pins and needles) in extremities, strange tastes or smells, dizziness, and excessive sweating or irritability. Dosages of trimethobenzamide and diphenhydramine were prepared from commercially available preparations of Tigan® and Benadryl®, respectively. A single dose for injection contained 200 mg of trimethobenzamide in 2 mL mixed with 50 mg of diphenhydramine in 1 mL. Injections were given by intramuscular injection (Gluteus muscle) to 113 individuals (two individuals were enlisted but not treated), where the dose delivered was adjusted according to body weight of the individual. A single dose for delivery by mouth (oral delivery) was prepared from commercially available capsules, containing 250 mg of trimethobenzamide and 25 mg diphenhydramine. The appropriate amount was prepared according to individual body weights and given orally to 5 individuals (individuals 70, 74, 78, 79, and 84 in Table 1).

All individuals showed reduction in symptoms within approximately 10 minutes of injection or ingestion for all individuals. All but 11 of the treated individuals were monitored over time. In 3 of these 11 individuals, mild headaches were reported approximately 7-10 days after treatment. However, there was evidence of possible sinusitis for these individuals at that time and they were not available for later follow up. It was determined in 5 individuals (unrelated to this study) having sinusitis without migraines that similar treatment with trimethobenzamide and diphenhydramine does not provide significant reduction in the headaches due to the sinusitis. Table 1 indicates the response to treatment for the remaining 107 individuals (includes 19 and 80, enlisted but not treated).

In all individuals, the migraine headache subsided and all symptoms were alleviated. These results, along with the lack of efficacy for treating sinusitis headache, suggest that the trimethobenzamide and diphenhydramine treatment is uniquely and specifically effective for migraine treatment. This is further supported in that headaches did not recur in other than these three individuals for up to 9 months, including those individuals who suffered migraines more than 10 times a month in the 3 months prior to treatment.

In some individuals, approximately 30% or less, some drowsiness was observed. However, the side effects normally associated with administration of either trimethobenzamide or diphenhydramine alone were not observed in any of the individuals. No adverse effects with regard to general health, or blood pressure, were noted by any of the treated individuals who suffered from migraines. Repeated administration of trimethobenzamide and diphenhydramine to non-migraine individuals caused no discernible effects with regard to blood pressure or general health. Overall, these results suggest that administering trimethobenzamide and diphenhydramine, either orally or by intra muscular injection, is a safe and effective treatment for migraines.

TABLE 1

Occurrence of migraine headaches pre and post treatment in individuals treated with trimethobenzamide and diphenhydramine. All doses were IM injection with the exception of those with (O) in the dose column (oral dose).

| Individual | | | Pre treatment condition | | | | Post treatment | | |
| --- | --- | --- | --- | --- | --- | --- | --- | --- | --- |
| # | Sex | Age | Headaches per month | Severity* | Average Duration | Symptoms** | Headaches per month | Months*** | # of doses |
| 1 | F | 24 | 1-2 | 3 | 24 | 1-2-3-4-6 | 0 | 9 | 1 |
| 2 | F | 48 | 15-18 | 2.5 | 24 | 1-2-4 | 0 | 9 | 1 |
| 3 | F | 43 | 1 | 3 | 24 | 1-2-4-6 | <<1**** | 6 | 1 |
| 4 | F | 79 | 8 | 3 | 24 | 1-2-3-6-7 | 0 | 9 | 1 |
| 5 | F | 35 | 10 | 2.5 | 24 | 1-2-4 | 0 | 9.5 | 1 |
| 6 | M | 31 | 6 | 3 | 24 | 1-2-3-4 | 0 | 8.5 | 1 |
| 7 | M | 37 | 6 | 3 | 24 | 1-2-4-6 | 0 | 8.5 | 1 |
| 8 | F | 24 | 1 | 3 | 24 | 1-2-3-6 | 0 | 8.5 | 1 |
| 9 | F | 19 | 11 | 2.5 | 24 | 1-3-4 | 0 | 8.5 | 1 |
| 10 | F | 47 | 12 | 3 | 24 | 1-2-3-4 | 0 | 8.5 | 1 |
| 11 | M | 49 | 8 | 2.5 | 24 | 1-2-4-7 | 0 | 8.5 | 1 |
| 12 | F | 43 | 1 | 2 | 24 | 1-2 | 0 | 8.5 | 1 |
| 13 | F | 32 | 9 | 2 | 24 | 1-2-4 | 0 | 8.5 | 1 |

TABLE 1-continued

Occurrence of migraine headaches pre and post treatment in individuals treated with trimethobenzamide and diphenhydramine. All doses were IM injection with the exception of those with (O) in the dose column (oral dose).

| | Individual | | Pre treatment condition | | | | Post treatment | | # of doses |
|---|---|---|---|---|---|---|---|---|---|
| # | Sex | Age | Headaches per month | Severity* | Duration | Symptoms** | Headaches per month | Months*** | |
| 14 | M | 24 | 10 | 2.5 | 24 | 1-2-5-6 | 0 | 8 | 1 |
| 15 | M | 29 | 10 | 3 | 24 | 1-2-4 | 0 | 8 | 1 |
| 16 | M | 33 | 2 | 2.5 | 24 | 1-2 | 0 | 8 | 1 |
| 17 | F | 10 | 10 | 2.5 | 24 | 1-2-3-4 | 0 | 8 | 1 |
| 18 | F | 34 | 10 | 2.5 | 24 | 1-2-3-4-6 | 0 | 8 | 1 |
| 19 | | | N/A | | | | | | |
| 20 | F | 34 | 5 | 3 | 24 | 1-2-4-7 | 0 | 8 | 1 |
| 21 | M | 32 | 1 | 2.5 | 24 | 1 | 0 | 8 | 1 |
| 22 | M | 39 | 1 | 3 | 24 | 1-2 | 0 | 8 | 1 |
| 23 | F | 35 | 9 | 3 | 24 | 1-2-3-4-6 | 0 | 8 | 1 |
| 24 | F | 34 | 10 | 3 | 24 | 1-2-3-5 | 0 | 8 | 1 |
| 25 | F | 10 | 5 | 2.5 | 24 | 1-2-4 | 0 | 8 | 1 |
| 26 | F | 10 | 8 | 2.5 | 24 | 1-2-3-4 | 0 | 8 | 1 |
| 27 | F | 47 | 9 | 2.5 | 24 | 1-2-3-4-7 | 0 | 8 | 1 |
| 28 | M | 21 | 4 | 2.5 | 24 | 1-2-4 | 0 | 8 | 1 |
| 29 | F | 22 | 10 | 2.5 | 24 | 1-2-3-4-6 | 0 | 8 | 1 |
| 30 | F | 65 | 4 | 2.5 | 24 | 1-2-3 | 0 | 8 | 1 |
| 31 | F | 45 | 6 | 3 | 24 | 1-2-4 | 0 | 8 | 1 |
| 32 | F | 27 | 1 | 2.5 | 24 | 1-2 | 0 | 7 | 1 |
| 33 | M | 69 | 8 | 2.5 | 24 | 1-2-4-7 | 0 | 7 | 1 |
| 34 | F | 22 | 5 | 3 | 24 | 1-2-3-6 | 0 | 7 | 1 |
| 35 | F | 43 | 1 | 3 | 24 | 1-3 | 0 | 7 | 1 |
| 36 | F | 49 | 6 | 3 | 24 | 1-2-3 | 0 | 7 | 1 |
| 37 | F | 30 | 2 | 3 | 24 | 1-2-3 | 0 | 7 | 1 |
| 38 | M | 31 | 8 | 3 | 24 | 1-2-3-6 | 0 | 7 | 1 |
| 39 | F | 25 | 10 | 2.5 | 24 | 1-2-3-6-7 | 0 | 7 | 1 |
| 40 | F | 35 | 9 | 3 | 24 | 1-2-3-4-6 | 0 | 7 | 1 |
| 41 | F | 34 | 4 | 2.5 | 24 | 1-2-6-7 | 0 | 7 | 1 |
| 42 | F | 34 | 8 | 2.5 | 24 | 1-2-3-4-7 | 0 | 7 | 1 |
| 43 | F | 35 | 8 | 2.5 | 24 | 1-2-3-5-6 | 0 | 7 | 1 |
| 44 | F | 26 | 1 | N/A | 48 | N/A | 0 | N/A | 1 |
| 45 | F | 39 | 7 | 2.5 | 24 | 1-2-3 | 0 | 7 | 1 |
| 46 | F | 27 | 8 | 2.5 | 24 | 1-2-3 | 0 | 7 | 1 |
| 47 | M | 20 | 1 | 2.5 | 24 | 1-5 | 0 | 7 | 1 |
| 48 | M | 48 | 9 | 2.5 | 24 | 1-2-3-4 | 0 | 7 | 1 |
| 49 | F | 38 | 9 | 3 | 24 | 1-2-3-7 | 0 | 7 | 1 |
| 50 | M | 46 | 8 | 2.5 | 24 | 1-2-3-4 | 0 | 7 | 1 |
| 51 | M | 15 | 6 | 2.5 | 24 | 1-2-4-6 | 0 | 6 | 1 |
| 52 | M | 26 | 2 | 2.5 | 24 | 1-2 | 0 | 6 | 1 |
| 53 | F | 9 | 1 | 2.5 | 24 | 1-5 | 0 | 6 | 1 |
| 54 | F | 23 | 2 | 2.5 | 24 | 1-2 | 0 | 5 | 1 |
| 55 | M | 14 | 8 | 2.5 | 24 | 1-2-4-6-7 | 0 | 5 | 1 |
| 56 | M | 16 | First Time 1 | 3 | 24 | 1-2-4 | 0 | 5 | 1 |
| 57 | M | 15 | First Time 1 | 3 | 24 | 1-2-3 | 0 | 5 | 1 |
| 58 | M | 26 | 2 | 2.5 | 24 | 1-2-3 | 0 | 5 | 1 |
| 59 | M | 38 | 9 | 2.5 | 24 | 1-2-3-5 | 0 | 5 | 1 |
| 60 | F | 28 | 9 | 2.5 | 24 | 1-2-3-4 | 0 | 5 | 1 |
| 61 | F | 46 | 7 | 2.5 | 24 | 1-2-3-4 | 0 | 5 | 1 |
| 62 | F | 40 | 8 | 2.5 | 24 | 1-2-3-4-6 | 0 | 5 | 1 |
| 63 | F | 40 | 8 | 2.5 | 24 | 1-2-3-4 | 0 | 5 | 1 |
| 64 | F | 30 | 8 | 3 | 24 | 1-2-3-4-6 | 0 | 5 | 1 |
| 65 | F | 51 | 2 | 3 | 24 | 1-2-3 | 0 | 5 | 1 |
| 66 | F | 38 | 8 | 3 | 24 | 1-2-3-4 | 0 | 5 | 1 |
| 67 | M | 15 | 8 | 3 | 24 | 1-2-3-4-5 | 0 | 5 | 1 |
| 68 | M | 45 | 8 | 3 | 24 | 1-2-3-4 | 0 | 5 | 1 |
| 69 | F | 24 | 8 | 3 | 24 | 1-2-3-4 | 0 | 5 | 1 |
| 70 | F | 29 | 1 | 2.5 | 24 | 1- | 0 | 5 | 1(O) |
| 71 | F | 13 | 4 | 2.5 | 24 | 1-2 | 0 | 5 | 1 |
| 72 | F | 46 | 7 | 3 | 24 | 1-2-3-4 | 0 | 5 | 1 |
| 73 | F | 47 | 8 | 3 | 24 | 1-2-3-4-7 | 0 | 5 | 1 |
| 74 | F | 33 | 4 | 2.5 | 24 | 1-2-3-4 | 0 | 5 | 1(O) |
| 75 | F | 35 | 8 | 3 | 24 | 1-2-3-4-5 | 0 | 5 | 1 |
| 76 | M | 64 | 8 | 2.5 | 24 | 1-2-3-4 | 0 | 5 | 1 |
| 77 | M | 33 | 6 | 2.5 | 24 | 1-2-3-4 | 0 | 5 | 1 |
| 78 | F | 52 | 8 | 2.5 | 24 | 1-2-3-4-6 | 0 | 5 | 1(O) |
| 79 | F | 44 | 8 | 2.5 | 24 | 1-2-3-4 | 0 | 5 | 1(O) |
| 80 | | | N/A | | | | | | |
| 81 | M | 40 | 8 | 2.5 | 24 | 1-2-3-4 | 0 | 5 | 1 |
| 82 | F | 19 | 8 | 2.5 | 24 | 1-2-3-4 | 0 | 5 | 1 |
| 83 | F | 57 | 5 | 2.5 | 24 | 1-2-3-5 | 0 | 5 | 1 |

TABLE 1-continued

Occurrence of migraine headaches pre and post treatment in individuals treated with trimethobenzamide and diphenhydramine. All doses were IM injection with the exception of those with (O) in the dose column (oral dose).

| Individual | | | Pre treatment condition | | | | Post treatment | | |
|---|---|---|---|---|---|---|---|---|---|
| | | | Headaches | | Average | | Headaches | | # of |
| # | Sex | Age | per month | Severity* | Duration | Symptoms** | per month | Months*** | doses |
| 84 | F | 35 | 4 | 3 | 24 | 1-2-3-4 | 0 | 5 | 1(O) |
| 85 | M | 29 | 8 | 3 | 24 | 1-2-3-4-7 | 0 | 5 | 1 |
| 86 | F | 55 | 8 | 2.5 | 24 | 1-2-3-4 | 0 | 5 | 1 |
| 87 | M | 35 | 8 | 2.5 | 24 | 1-2-3-4 | 0 | 5 | 1 |
| 88 | F | 32 | 11 | 2.5 | 24 | 1-2-3-4-6-7 | 0 | 4 | 1 |
| 89 | | | Constant | 1-2-3 | 24 | 1-2-3-4-5-6-7 | 0 | 4 | 1 |
| 90 | F | 40 | 4 | 2.5 | 24 | 1-2-3 | 0 | 4 | 1 |
| 91 | F | 38 | Every Day | 1-2-3 | 24 | 1-2-3-4 | 0 | 4 | 1 |
| 92 | F | 53 | 8 | 2.5 | 24 | 1-2-3-4 | 0 | 4 | 1 |
| 93 | M | 58 | 8 | 2.5 | 24 | 1-2-3-4 | 0 | 4 | 1 |
| 94 | F | 9 | 8 | 2.5 | 24 | 1-2-3-4-6 | 0 | 4 | 1 |
| 95 | F | 65 | 6 | 2.5 | 24 | 1-2-3-4 | 0 | 2 | 1 |
| 96 | M | 19 | 8 | 2.5 | 24 | 1-2-3-4-5 | 0 | 2 | 1 |
| 97 | M | 26 | 1 | 2.5 | 24 | 1-2-3-4 | 0 | 2 | 1 |
| 98 | F | 10 | 2 | 2.5 | 24 | 1-2-3 | 0 | 2 | 1 |
| 99 | F | 56 | 8 | 1-2-3 | 24 | 1-2-3-4-7 | 0 | 2 | 1 |
| 100 | F | 37 | 4 | 2.5 | 24 | 1-2-3-4 | 0 | 2 | 1 |
| 101 | F | 33 | 2 | 3 | 24 | 1-2-3-4-5-6 | 0 | 2 | 1 |
| 102 | F | 14 | 1 | 3 | 24 | 1-2-3-4 | 0 | 2 | 1 |
| 103 | F | 13 | 7 | 2.5 | 24 | 1-2-3-4-5 | 0 | 2 | 1 |
| 104 | F | 13 | 8 | 2.5 | 24 | 1-2-3-4 | 0 | 2 | 1 |
| 105 | F | 27 | 8 | 2.5 | 24 | 1-2-3-4-5 | 0 | 1 | 1 |
| 106 | F | 19 | 8 | 2.5 | 24 | 1-2-3-4-5 | 0 | 1 | 1 |
| 107 | M | 31 | 6 | 2.5 | 24 | 1-2-3-4-6 | 0 | 1 | 1 |
| 108 | M | 41 | 8 | 2.5 | 24 | 1-2-3-4 | 0 | 1 | 1 |
| 109 | F | 23 | 4 | 2.5 | 24 | 1-2-3-4 | 0 | 2 wks | 1 |

*Severity 1 = mild, 2 = moderate, 3 = severe
**Symptoms 1 = throbbing headache, 2 = photophobia or visual disturbance 3 = earache or noise disturbance, 4 = nausea or vomiting, 5 = abdominal discomfort, 6 = limpness in extremities, 7 = pins and needles in extremities.
***Months without a headache following a single treatment.
****This individual had one headache in 9 months (at 6 months).

What is claimed as new and desired to be protected by Letters Patent of the United States is:

1. A method for the treatment and diminishment of occurrences of migraine headaches comprising administering to an individual in need thereof a unit dose of a composition comprising trimethobenzamide and diphenhydramine, wherein the unit dose comprises 25 mg to 500 mg trimethobenzamide and 5 mg to 150 mg diphenhydramine, and wherein the administration diminishes occurrence of migraine headaches in the individual for at least two weeks.

2. The method of claim 1, wherein the period of time is at least one month.

3. The method of claim 1, wherein treatment is prophylactic and wherein the unit dose is administered about one time per month.

4. The method of claim 1, wherein the composition is formulated for non-parenteral delivery.

5. The method of claim 4, wherein the composition is formulated for oral delivery.

6. The method of claim 5, wherein the unit dose comprises 250 mg trimethobenzamide and 25 mg diphenhydramine.

7. The method of claim 1, wherein the composition is formulated for parenteral delivery.

8. The method of claim 7, wherein parenteral delivery is via intra venous delivery or injection.

9. The method of claim 8, wherein the parenteral delivery is via injection.

10. The method of claim 9, wherein the unit dose comprises 200 mg trimethobenzamide and 50 mg diphenhydramine.

11. The method of claim 1, wherein the composition is a pharmaceutical composition further comprising one or more pharmaceutically acceptable excipients, adjuvants, diluents or stabilizers.

12. The method of claim 4, wherein the composition is a pharmaceutical composition further comprising one or more pharmaceutically acceptable excipients, adjuvants, diluents or stabilizers.

13. The method of claim 7, wherein the composition is a pharmaceutical composition further comprising one or more pharmaceutically acceptable excipients, adjuvants, diluents or stabilizers.

14. The method of claim 1, wherein the unit dose of trimethobenzamide and diphenhydramine is provided in separate dosage forms.

15. The method of claim 1, wherein the unit dose of trimethobenzamide and diphenhydramine is formulated as a mixture.

16. The method of claim 1, wherein the trimethobenzamide and diphenhydramine are administered simultaneously.

17. The method of claim 1, wherein the unit dose comprises 250 mg to 300 mg trimethobenzamide and 10 mg to 100 mg diphenhydramine.

18. The method of claim 9, wherein the injection is intra muscular.

19. The method of claim 1, wherein the administration diminishes occurrence of migraine headaches in the individual for at least five months.

20. The method of claim 1, wherein the administration diminishes occurrence of migraine headaches in the individual for at least nine months.

21. The method of claim 1, wherein the administration does not cause diarrhea, hypotension, or a combination thereof in the individual.

* * * * *